(12) United States Patent
Kelly et al.

(10) Patent No.: US 8,137,305 B2
(45) Date of Patent: Mar. 20, 2012

(54) PROGRAMMABLE ELECTRIC BREAST PUMP

(76) Inventors: Patricia A. Kelly, Burbank, CA (US);
Joan P. Ortiz, Burbank, CA (US); Leslie Beckwith, La Mirada, CA (US)

( * ) Notice: Subject to any disclaimer, the term of this patent is extended or adjusted under 35 U.S.C. 154(b) by 1297 days.

(21) Appl. No.: 11/656,145

(22) Filed: Jan. 22, 2007

(65) Prior Publication Data
US 2008/0177224 A1    Jul. 24, 2008

(51) Int. Cl.
*A61M 1/06* (2006.01)
(52) U.S. Cl. .......................................... 604/74
(58) Field of Classification Search .............. 604/74–76, 604/317, 346
See application file for complete search history.

(56) References Cited

U.S. PATENT DOCUMENTS

| | | |
|---|---|---|
| 4,772,262 A | 9/1988 | Grant et al. |
| 4,799,922 A | 1/1989 | Beer et al. |
| 4,961,726 A | 10/1990 | Richter |
| 5,071,403 A | 12/1991 | Larsson |
| 5,380,280 A | 1/1995 | Peterson |
| 5,419,768 A | 5/1995 | Kayser |
| 5,571,084 A | 11/1996 | Palmer |
| 5,624,394 A | 4/1997 | Barnitz et al. |
| 5,676,525 A | 10/1997 | Berner et al. |
| 5,795,328 A | 8/1998 | Barnitz et al. |
| 5,810,772 A | 9/1998 | Niederberger |
| 5,885,246 A | 3/1999 | Ford |
| 5,902,267 A | 5/1999 | Medo |
| 5,954,690 A | 9/1999 | Larsson |
| 6,045,529 A | 4/2000 | Nüesch |
| 6,383,163 B1 * | 5/2002 | Kelly et al. ........... 604/74 |
| 6,547,756 B1 * | 4/2003 | Greter et al. .......... 604/74 |
| 6,663,587 B2 | 12/2003 | Silver et al. |
| 6,932,790 B2 * | 8/2005 | McKendry et al. ...... 604/74 |

(Continued)

FOREIGN PATENT DOCUMENTS

DE    38 20 211 A    6/1988

OTHER PUBLICATIONS

Zoppou, Ph.D., Christopher et al., "Comparing Breastfeeding and Breast Pumps using a Computer Model," J Hum Lact 13(3), Mar. 25, 1997, pp. 195-202.

(Continued)

*Primary Examiner* — Matthew F Desanto
(74) *Attorney, Agent, or Firm* — Kenneth L. Green (57) ABSTRACT

A programmable electric breast pump system includes a vacuum pump pneumatically coupled to breast cups and a vacuum relief valve bypassing the vacuum pump. A controller receives command input from a vacuum level selector and a vacuum rate selector, and feedback from a pressure sensor measuring vacuum in the breast cups. In response, the controller cycles the relief valve between minimum and maximum vacuum setpoints to create a periodic vacuum pulse in the breast cups. By adjusting the vacuum min/max levels and vacuum rate, a user may change the strength of the pulse after let-down, or synchronize the frequency of the pulse with the natural refractory time of a lactating breast. Related methods for operating a breast pump mimic the suckling cycle of a nursing infant and may include steps for bypassing a vacuum pump with a vacuum relief valve, selecting a vacuum rate and a vacuum level, driving a vacuum pump at the selected vacuum rate, cycling the relief valve according to the vacuum level, and adjusting the vacuum level until the vacuum pulses in phase with a natural refractory time.

31 Claims, 8 Drawing Sheets

U.S. PATENT DOCUMENTS

| | | | |
|---|---|---|---|
| 7,658,737 B2 * | 2/2010 | Hartlaub et al. | 604/891.1 |
| 2002/0193731 A1 * | 12/2002 | Myers et al. | 604/74 |
| 2005/0059928 A1 * | 3/2005 | Larsson | 604/74 |

OTHER PUBLICATIONS

Vincent, Monty E., et al., "Evaluation of Vacuumi Suction Safety Devices in Preventing Transmission of Human Virus Pathogen," American Clink Laboratory, Jan. 1989, 4 pages.

Blenkharn, J. Ian, "Infection Risks From Electrically Operated Breast Pumps," Journal of Hospital Infection, 1989, 13, pp. 27-31.

Donowitz, Frederic J., "Contaminated Breast Milk: A Source of *Klebsiella* Bacteremia in a Newborn Intensive Care Unit," The University of Chicago, Review of Infectious Diseases, vol. 3, No. 4, Jul.-Aug. 1981, pp. 716-720.

Fewtrell, M.D., Mary S., "Randomized Trial Comparing the Efficacy of a Novel Manual Breast Pump with a Standard Electric Breast Pump in Mothers Who Delivered Preterm Infants," Pediatrics, vol. 107, No. 6, Jun. 2001, pp. 1291-1297.

* cited by examiner

PROGRAMMABLE ELECTRIC BREAST PUMP

This application is related to co-pending U.S. application Ser. No. 10/644,199, which is fully incorporated herein by reference.

BACKGROUND OF THE INVENTION

1. Field of the Invention

The present invention relates generally to automatic breast pumps. More specifically, the invention relates to apparatus and related methods for extracting milk from a human breast using adjustable controls that simulate the action of a nursing infant.

2. Description of Related Art

Most prior art breast pumps designed for extracting milk are concerned only with controlling the rate at which a negative pressure is applied to the breast and, in some cases, the amount of negative or vacuum pressure. An example of an electric breast pump which does more than this is illustrated in the U.S. Pat. No. 6,383,163 granted May 7, 2002 to two of the three named joint inventors of the present invention. The disclosure of U.S. Pat. No. 6,383,163 is expressly incorporated herein by reference.

Although the prior art breast pumps and, specifically, the prior art breast pump described and claimed in U.S. Pat. No. 6,383,163 are effective, they also have a number of shortcomings. For example, most prior art breast pumps only allow a mother to express her milk by applying a uniform vacuum pressure (or vacuum pressure profile) to the face of the breast. This simple approach does not effectively simulate the natural suckling of a nursing infant. Without effective simulation, the pump does not extract the milk as efficiently as possible. As a result, a longer pumping period is required, which increases the physical demands on the mother. These demands may discourage working mothers, or mothers still recovering from childbirth, from thoroughly completing the expression. Incomplete or improper expression of the milk may lead to engorgement of the breasts, mastitis, or infection.

In a natural suckling cycle, refractory time of the breast plays an important role in optimizing the efficiency of milk extraction. The refractory time is that part of the nursing cycle that begins after milk has been drawn from ducts within the breast, and ends when the depleted portions of the milk ducts refill. One invention that accounts for this refractory time is disclosed in U.S. patent application Ser. No. 10/644,199, assigned to the assignee of the present invention. The '199 application discloses a breast pump that draws a vacuum in periodic pulses at a frequency that may be adjusted by the mother to track her physiological refractory time.

Nursing an infant, however, is a biological process that is not so easily modeled with mathematical precision. Many conditions can change during expression of the milk. Perhaps the most obvious example is the onset of the let-down, or milk-ejection reflex. Research has shown that prior to let-down, an infant will suck at an elevated rate in the range of 72 to 120 sucks per minute. After let-down, when a satisfactory flow of milk is obtained, the infant relaxes the rate down to around 60 sucks per minute. The vacuum drawn by a suckling infant may vary between 18 mmHg and 200 mmHg. Prior to let-down, an infant typically applies a greater suction force than after let-down. In addition, as the store of milk in the alveoli diminishes, the infant may apply a higher suction force to sustain the flow.

The optimal refractory times, vacuum pressures, and vacuum pressure profiles will vary among different mothers. What is needed, then, is a breast pump that can be easily customized to optimize the efficiency of expression over a wide range of conditions.

SUMMARY OF THE INVENTION

A programmable electric breast pump system includes a vacuum pump pneumatically coupled to breast cups and a vacuum relief valve bypassing the vacuum pump. The system includes an electronic controller, a vacuum level selector, and a vacuum rate selector. The vacuum level selector and vacuum rate selector may be manipulated by a user to provide variable command input to the controller. The vacuum level selector changes maximum and/or minimum vacuum pressure setpoints. The vacuum rate selector changes the speed of the vacuum pump. A vacuum sensor senses pressure in the breast cups and feeds back a pressure signal to the controller. In response, the controller cycles the relief valve between the minimum and maximum vacuum pressure setpoints to create a periodic vacuum pulse in the breast cups. By adjusting the vacuum level and vacuum rate, a user may change the strength and/or frequency of the vacuum pulse applied to the breast cups to achieve a desired comfort level, to lower the strength after let-down, or to synchronize the pulse with the natural refractory time of a lactating breast. A related method includes steps for bypassing a vacuum pump with a vacuum relief valve, selecting a vacuum rate and a vacuum level, driving a vacuum pump at the selected vacuum rate, and cycling the relief valve according to the vacuum level. Additional steps may be provided for adjusting the vacuum level until the vacuum drawn in the breast cups pulses in phase with a natural refractory time to mimic the suckling cycle of a nursing infant.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein.

DETAILED DESCRIPTION OF THE PREFERRED EMBODIMENTS

The breast pump of the present invention continuously monitors the vacuum pressure that is applied to the milk collection system, i.e., the breast cups, by utilizing an electronic control system that includes a solid state pressure sensor and associated circuitry. The information provided by the sensor completes a feedback loop to the control system, which actuates an electronic valve in the vacuum system to create a suction cycle that mimics the action of a suckling infant. In addition, the breast pump is designed to provide fail-safe operation by continuously monitoring the pressure applied to the breast cups, by monitoring the time elapsed during a pumping session, and by monitoring the internal temperature of the control circuits.

Figure 1:
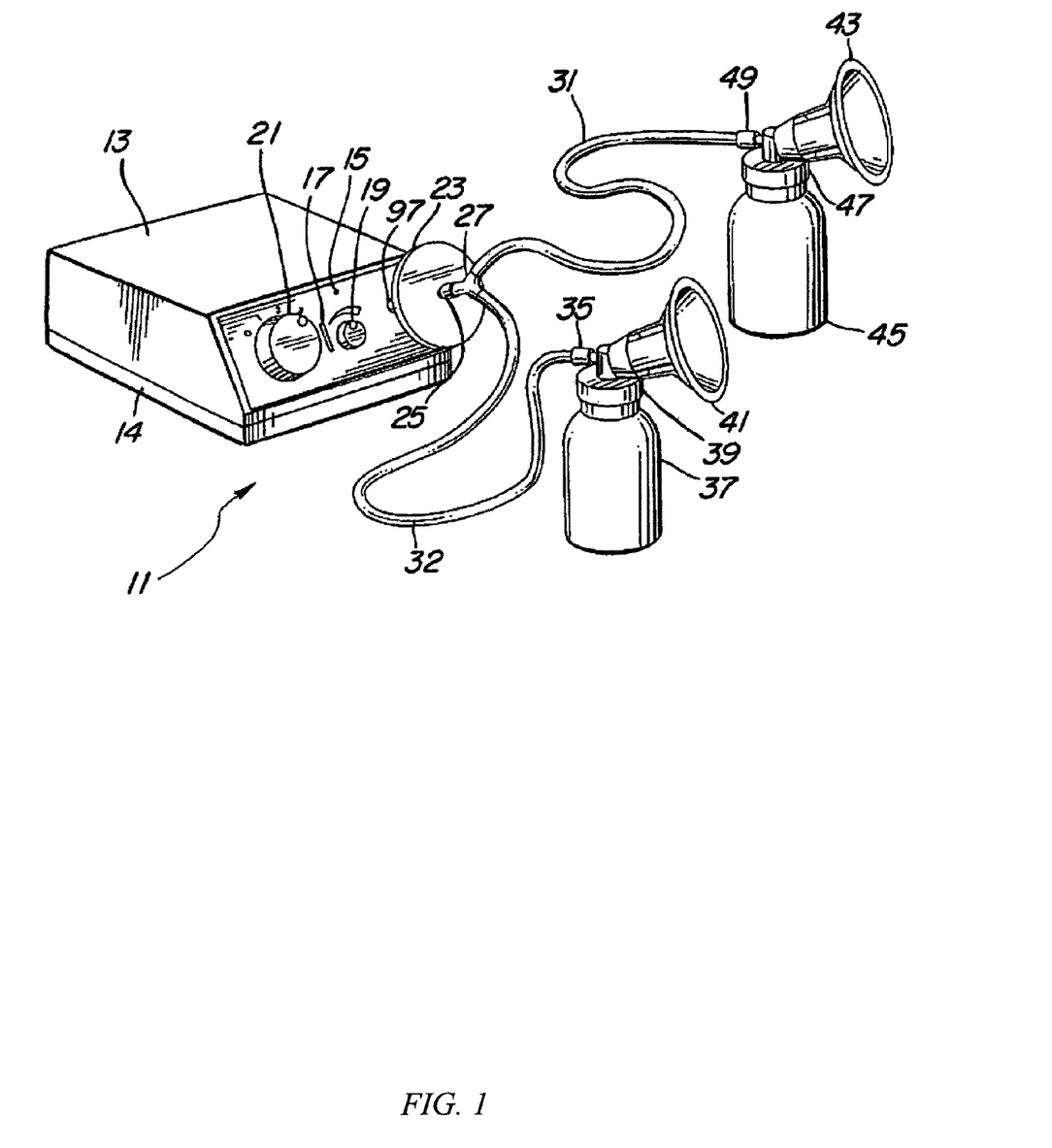
FIG. 1 is a perspective illustration of a programmable electric breast pump system according to one embodiment of the present invention.

Referring now to FIG. 1, an electric programmable breast pump system 11 according to the present invention is illustrated as contained within a housing having a top 13 and a base 14, preferably made of a light-weight sheet metal or plastic. The housing contains a pump control circuit and sensing elements which will be hereinafter described. The housing top 13 has manually operable controls for the user such as a vacuum level selector 19 and a combination on-off switch and vacuum rate selector 21. In one embodiment, selectors 19 and 21 are potentiometers with control knobs. A timer indicating light 17 and on-off fault indicator LED 15 may also be provided to provide indication to the user regarding the function of the breast pump system 11. The time indicating light 17 indicates time lapsed in an expression session.

A disposable isolation filter 23 is shown attached to a pump connector 97 through the front panel of the housing top 13. A short length of tubing 25 attaches to the inlet side of filter 23. Because the illustration is for a two breast cup system, a Y-connector 27 may be added to connect tube line 25 to a pair of vacuum lines 31, 32 which lead to respective collection bottles and breast cups. A vacuum line 31 may be connected to a breast cup 43 by way of a tube connector 49. Vacuum tube or line 32 may be connected to breast cup 41 by way of a tube connector 35. Each breast cup 43 and 41 is preferably symmetrical and made of a soft flexible material, such as silicone rubber constructed to provide a controlled collapse in operation. Each breast cup may be shaped to comfortably fit over the human teat and a portion of the breast. Each breast cup is associated with its respective collection bottle. Breast cup 41 is shown connected to vacuum line 32, and also connects to the interior of collection bottle 37 by a removable cap 39. Likewise, breast cup 43 is connected to connection bottle 45 by a removable cap 47.

Figure 2:
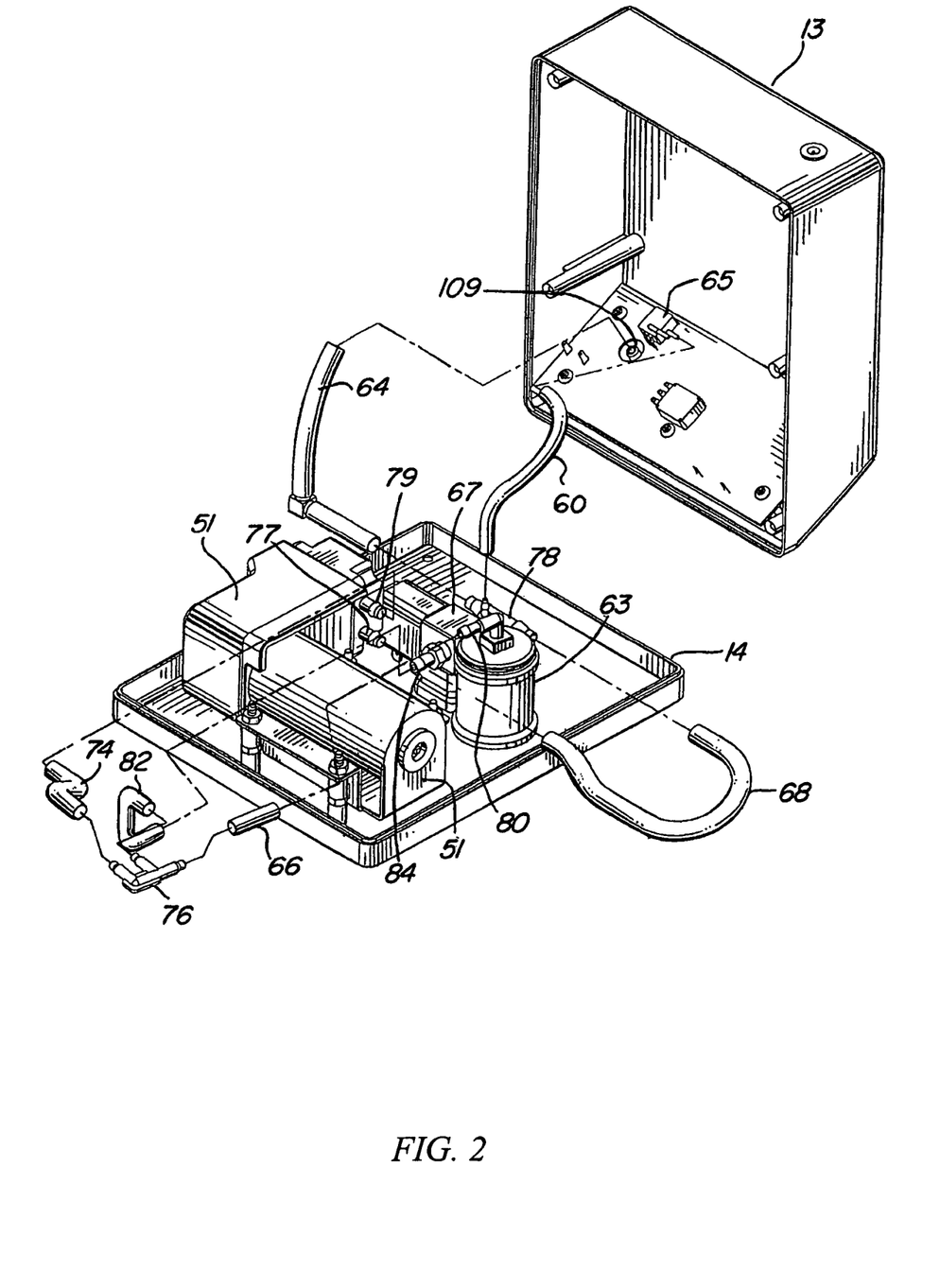
FIG. 2 is a perspective exploded illustration of one embodiment of a control unit according to the invention for containing pumping and control elements.

FIG. 2 illustrates an exploded perspective of the inside of the housing with the top 13 separated from the bottom 14. Within the housing are the various components that make up the pump control circuit and other mechanical and electrical components. A motor-driven piston vacuum pump 51 is shown mounted to the bottom 14 of the housing. In another embodiment, pump 51 may be a diaphragm pump, such as a Koge Electronics type KPV vacuum pump. The inlet side 77 of pump 51 may be connected by way of a vacuum line 68, four-way connector 78 and vacuum line 64 to a back side connection 109 of isolation filter connector 97.

In addition to connecting vacuum lines 68 and 64 together, four-way connector 78 may connect to the input side (not shown) of vacuum relief valve 67. In one embodiment, vacuum relief valve 67 may be a Koge Electronics type KSV solenoid valve. The output side 84 of vacuum relief valve 67 may be connected by way of line 82, T-connector 76 and line 66 to the input 80 of the exhaust filter 63. The output side 84 of vacuum relief valve 67 may also be connected by way of line 82, T-connector 76 and line 74 to the output end 79 of the pump 51. A vacuum sensor 65 may be mounted to the top 13 of the housing. Vacuum sensor 65 senses vacuum level in the system, for example, through four-way connector 78 over line 60.

Figure 3:
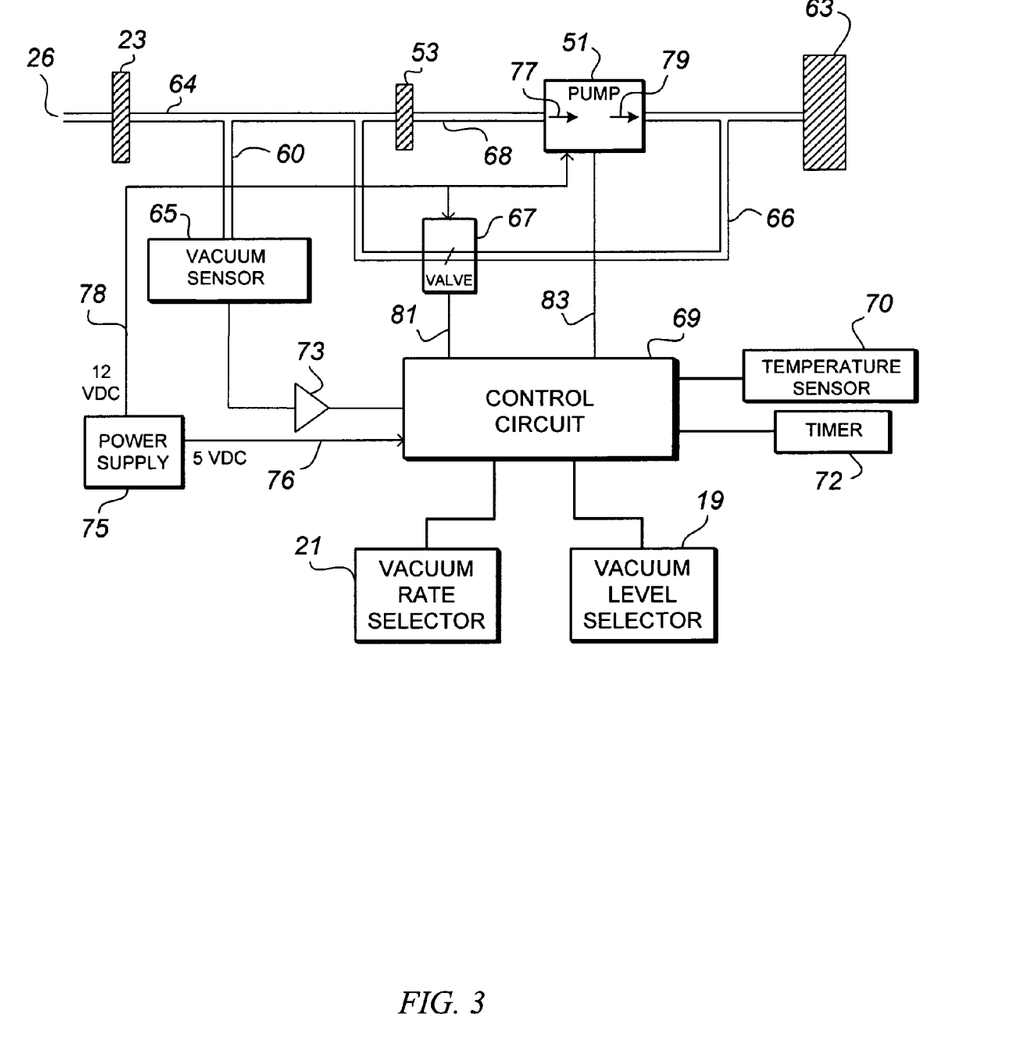
FIG. 3 is a block diagram showing a control system for a programmable electric breast pump according to the invention.

The block diagram of FIG. 3 illustrates the operation of mechanical and electrical components within the programmable electric breast pump system. Electrical power for the system is provided by a power supply 75. In the embodiment shown, power supply 75 provides two DC outputs: a 5 VDC output for powering the active electronics within a programmable control circuit 69, and a 12 VDC output for powering an electric pump 51 and an electrically operated valve 67. Power supply 75 may be a battery bank, or an AC/DC converter receiving power from a standard 120 VAC outlet. In another embodiment, power supply 75 may include a battery charger coupled to a bank of rechargeable batteries, or a battery holder that holds one or more standard commercial batteries such as ten AA batteries.

Programmable control circuit 69 provides central control for the system. Control circuit 69 may be a microprocessor, microcontroller, FPGA, ASIC, or the like, and may include integral memory for storing executable control algorithms. In one embodiment, control circuit 69 receives five input signals. The first two of these are command inputs from vacuum level selector 19 and vacuum rate selector 21. In one embodiment, vacuum rate selector 21 includes as on/off function that turns the system on or off. In addition, vacuum rate selector 21 may provide a variable input signal to control circuit 69. Vacuum level selector 19 may also provide a variable input to control circuit 69. In one embodiment, a variable input signal to control circuit 69 may be a voltage that varies continuously or in discrete steps according to a control knob position.

The next two inputs are sensor inputs from vacuum sensor 65 and temperature sensor 70. Vacuum sensor 65 senses vacuum pressure in vacuum line 64 through conduit 68, and transmits a signal representing the sensed pressure to control circuit 69. In one embodiment, vacuum sensor 65 is a silicon packaged piezoresistive pressure sensor. In one example, vacuum sensor 65 may be a Fujikura type XFHM vacuum sensor. Temperature sensor 70 senses temperature within the housing of breast pump system 11. Temperature sensor 70 may provide a means for sensing an abnormally high or unsafe operating temperature, and for transmitting a signal representing the sensed temperature to control circuit 69. If the sensed temperature exceeds a predetermined maximum safe operating temperature, control circuit 69 may stop vacuum pump 51, or otherwise shut down the operation of the breast pump system. One example of a temperature sensor 70 is an integrated circuit type LM50C sensor manufactured by National Semiconductor.

The fifth input to control circuit 69 may be a timing or clock input provided by a timer 72. Timer 72 may be a well-known type and will not be described herein in further detail. In one embodiment, timer 72 may be integral to control circuit 69.

Timer 72 provides the clock input required to synchronize the operation of control circuit 69, and to provide a means for control circuit 69 to measure elapsed times.

In one embodiment, control circuit 69 transmits two output signals. The first of these may be a drive signal transmitted over signal line 83 to vacuum pump 51. The pump drive signal received from control circuit 69 may vary according to the position of vacuum rate selector 21. As the selector is adjusted to increase vacuum, control circuit 69 responds by outputting a drive signal that causes a commensurate increase in energy delivered by pump 51. One example of such a drive signal is a square wave having a variable pulse width, or duty cycle. When vacuum rate selector 21 is switched on and to a minimum position, control circuit 69 may output a fractional square wave, such as square wave having a 50% duty cycle. With vacuum rate selector 21 at a maximum position, control circuit may output a 100% duty cycle signal to pump 51. Intermediate position of vacuum rate selector 21 may cause a corresponding adjustment in the duty cycle of the drive signal. Other drive signals may be used, such as a DC signal having a voltage that varies according to selector position, or an AC pulse having a shape other than square.

Pump 51 is shown connected to vacuum line 64 at its input side 77. A biological isolation filter 23 may also connect to vacuum line 64. The input 26 of biological filter 23 is connected to breast cups 43 and 41 (FIG. 1) by way of their respective vacuum lines 31 and 32. Thus, when receiving the drive signal from control circuit 69, pump 51 may vary its speed accordingly, causing the suction rate at input 77 to vary in proportion to the position of vacuum rate selector 21.

A second biological filter 53 may be located at the physical input 77 of pump 51 between the pump input 77 and vacuum relief valve 67. A third exhaust filter 63 is located at the physical output 79 of pump 51 after the output line 66 of vacuum relief valve 67. The vacuum line 66 connects or shunts around pump 51 from the input side of biological filter 53 to the output side of pump 71, at the input side of the third biological exhaust filter 63.

Vacuum relief valve 67 may be connected into the shunt vacuum line 66 to provide a means for bypassing pump 51. Valve 67 may be controlled over line 81 by control circuit 69. In one embodiment, valve 67 may assume either an open state or a closed state. When pump 51 is running and control circuit 69 causes valve 67 to close, vacuum pressure increases in vacuum line 64 and in breast cups 41 and 43. When control circuit causes valve 67 to open, pump 51 is bypassed, and pressure in vacuum line 64 begins rising to an ambient pressure level at exhaust filter 63.

The signal transmitted from vacuum sensor 65 may be amplified by a sensor amplifier 73 before being input to control circuit 69. Normal operation of the breast pump is controlled according to the positions of vacuum rate selector 19 and vacuum level selector 21, and on feedback received by control circuit 69 from vacuum sensor 65.

The function of the breast pump in the housing is to provide a vacuum at male connector 97 to which the biological isolation filter 23 is removably connected. The vacuum lines connected to the biological isolation filter 23 carry the vacuum to the breast cups. The breast pump system may be started by switching vacuum rate selector 21 from an off position to an on position. At startup, control circuit 69 causes valve 67 in vacuum line shunt 66 to be held open for a short time (counted by timer 72) so that the vacuum circuit is open to the atmosphere through exhaust filter 63. This prevents a vacuum level from being built up instantaneously. Also at startup, control circuit 69 outputs a drive signal to pump 51 according to the position of vacuum rate selector 21. Within a second or two after startup, control circuit 69 closes valve 67. With the breast cups positioned against a user's breasts, and with the vacuum lines 31 and 32 attached to the pump by way of the first biological isolation filter 23, the vacuum circuit for the system is closed. Pump 51 then draws a vacuum in the system. The vacuum sensor 65 attached to the vacuum line 64 continuously monitors the level of vacuum in the system. The vacuum sensed by sensor 65 is a good indicator of the vacuum being applied to breast cups 41 and 43. When the vacuum level reaches a maximum level set by the vacuum level selector 19, control circuit 69 causes valve 67 to open for a short period of time (counted by timer 72) to cause the vacuum level in breast cups 41 and 43 to drop. When the vacuum pressure has dropped to a level at or below a minimum vacuum level, control circuit 69 will cause valve 67 to again close, thereby allowing the vacuum to increase again. In this fashion, control circuit 69 cycles a vacuum pump bypass signal to valve 67 in response to the selected vacuum rate signal and the selected vacuum level signal.

In one embodiment, the minimum vacuum level is a predetermined value stored in the memory of control circuit 69. In another embodiment, the minimum vacuum level changes as a function of the maximum vacuum level set by the vacuum level selector. In another embodiment, a microcontroller 69 sets the minimum and maximum vacuum pressures according to data stored in a lookup table. In yet another embodiment, a microcontroller 69 calculates the minimum and maximum vacuum pressures by executing an algorithm.

The cycling of valve 67 on and off repeats until the system is turned off by adjusting vacuum rate selector 21 to the off position. During the time that valve 67 is closed and the vacuum rate selector is turned on, vacuum pressure is being applied to the breasts contained within the flexible breast cups. During the time that valve 67 is open, no pressure is applied to the breasts. Thus, by cycling valve 67 open and closed, control circuit 69 creates a pulsing vacuum pressure within breast cups 41 and 43. With vacuum level selector 19 and vacuum rate selector 21 in fixed positions, a periodic suction cycle results. The suction cycle consists of a vacuum pulse and an electronic refractory time. Vacuum is drawn during that portion of the suction cycle when the vacuum pulse is applied. Vacuum is relieved during the remaining portion, which is the electronic refractory time.

The control system of the present invention allows a user to synchronize the suction cycle with the physiological refractory time that is inherent in the normal function of a lactating breast. By physiological refractory time is meant that part of a feeding or pumping cycle that starts after the milk has been ejected from the breast and ends with the refilling of the breast chambers with milk prior to the next pressure-induced ejection of milk. Synchronization of the suction cycle of the vacuum pump to the natural refractory time of breast may be achieved by a user adjusting vacuum level selector 19 and vacuum rate selector 21 until an optimal milking rate is achieved, i.e. when the electronic refractory time is in phase with the natural refractory time to allow the breast chambers to refill in time for the next vacuum pulse. The result is a substantial increase in the expression rate of milk, and a concomitant reduction in physical demands on the mother.

The electronic refractory time is a function of both the vacuum level set by vacuum level selector 19, and vacuum rate set by vacuum rate selector 21. The electronic refractory time is the period from the end of a vacuum pulse applied by the control circuit 69 to valve 67 that causes the valve to open to relieve vacuum in the breast cup, to the beginning of the next vacuum pulse. When the next vacuum pulse is applied by the control circuit, the valve closes and vacuum pressure increases. The duration, Pv, of the vacuum pulse is the time required for vacuum pump 51 to raise vacuum pressure in the system from the minimum level to the selected maximum level. With vacuum level selector 19 in a fixed position, Pv may be shortened by raising the vacuum rate, i.e. by selecting a higher rate on vacuum rate selector 21, or Pv may be lengthened by lowering the vacuum rate on vacuum rate selector 21. Conversely, with vacuum rate selector 21 in a fixed position, Pv may be lengthened by raising the vacuum level, i.e. by selecting a higher maximum vacuum on vacuum level selector 19, or Pv may be shortened by lowering the maximum vacuum level on vacuum level selector 19. Thus, a user may "tune in" an optimal electronic refractory time by connecting the breast cups, turning the system on, and adjusting one or both selectors until the an optimal expression rate is achieved. It has been found that the ability of the user to adjust the electronic refractory time, to suit the individual physiological differences of the user, adds considerably to the comfort level of the user. In one embodiment, the vacuum cycle can be adjusted by the user in a preferred range of 28-60 cycles/minute.

Recall that control circuit 69 contains, or is coupled to, timer 72 which may provide timing pulses for control circuit synchronization and other counting functions. One such counting function is a time-out function that provides a safety feature for a user. A counter (not shown) within control circuit 69 may start counting the first time the vacuum sensed by vacuum sensor 65 reaches the maximum level set by the vacuum level selector. The start of the count may be indicated on the front panel display 17. The display on the front panel may assist the user in remembering not to exceed the recommended amount of time for one session of expressing milk using the breast pump system. In one example, the recommended amount of time at one sitting should not exceed 20 minutes. The timer in control circuit 69 may be reset when the system is powered off.

Timer 72 may provide diagnostic functions as well. In one embodiment, a controller (e.g. control circuit 69) may count the time elapsed on timer 72 between closing valve 67 and reopening valve 67 within a single cycle. If the time elapsed is less than a predetermined minimum closure time, the controller may stop the vacuum pump. Such a condition is a likely indication of an obstruction somewhere in the pneumatic lines. In another embodiment, if the time elapsed is greater than a predetermined maximum closure time, the controller may stop the vacuum pump. This condition is a likely indication of a leak somewhere in the pneumatic lines. In these embodiments, the predetermined minimum and maximum closure times may be stored in a memory accessible by the controller, or programmed into an algorithm executed by the controller.

Another safety feature that may be provided by control circuit 69 is a low pressure shut-off threshold, or equivalently, a maximum vacuum pressure threshold. The low pressure shut-off threshold may be permanently fixed or programmed into control circuit 69, at a vacuum pressure higher than the highest maximum vacuum pressure obtainable using vacuum level selector 19. When the low pressure shut-off threshold is sensed by vacuum sensor 65, control circuit 69 shuts down the pump. This safety feature would actuate, for example, if valve 67 fails closed, if pump 51 runs at an excessive speed, or if for some other reason vacuum pressure cannot be relieved in the system.

The vacuum pulse created by the breast pump system may be ideally suited for use with breast cups that collapse in a progressively controlled way that simulates the suckling action of a nursing infant. Progressively collapsible breast cups collapse in response to an applied vacuum pressure such that the areola area of the breast is squeezed before the teat. Breast cups of this type are disclosed in co-pending U.S. patent application Ser. No. 10/644,199.

Figure 4:
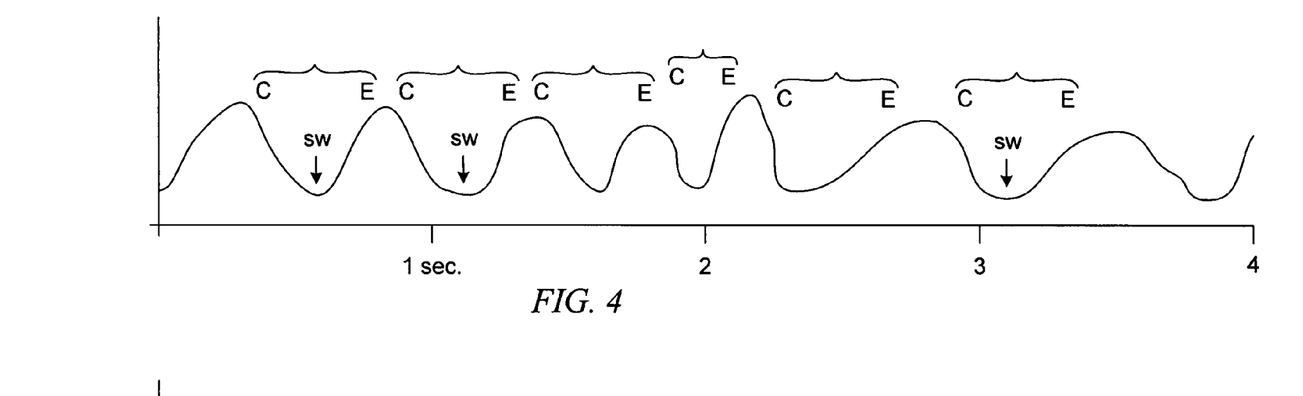
FIG. 4 is a graph of pressure vs. time, illustrating a typical natural respiratory cycle of a nursing infant.

FIG. 4 shows a respiratory cycle of a suckling infant. The graph is based on information recorded in Weber, et al., "An Ultrasonic Study of the Organisation of Suckling and Swallowing by Newborn Infants," Developmental Medicine & Child Neurology, 1986. The horizontal direction indicates time. The vertical axis indicates pressure, where a rising segment corresponds to pressure building in the areola as the infant inspires, drawing a suction on its mother's breast. The rising segment may also represent the natural refractory time of a lactating breast. A falling segment indicates a pressure reduction in the areola as milk is drawn out while the infant expires. Each trough, indicated by SW, corresponds to a time when the infant swallows the milk. Points labeled C correspond to times when the mother's nipple begins to compress. Points labeled E correspond to times when the nipple is fully expanded.

As indicated in FIG. 4, the respiratory cycle (or suck-swallow cycle) of a nursing infant exhibits periodic behavior. The four-second trace shown in the figure was derived from a test conducted by Weber et al., in which the infant under test completed 26 suck-swallow cycles in 15 seconds. This example indicates a typical respiratory cycle between about 100 and about 120 cycles per minute. Actual respiratory cycles may vary within this or some other range, depending on the natural refractory time of the mother, and may also vary for each mother-infant pair. Generally, the respiratory cycle closely tracks the natural refractory cycle of the mother's lactating breast during nursing.

Figures 5, 6:
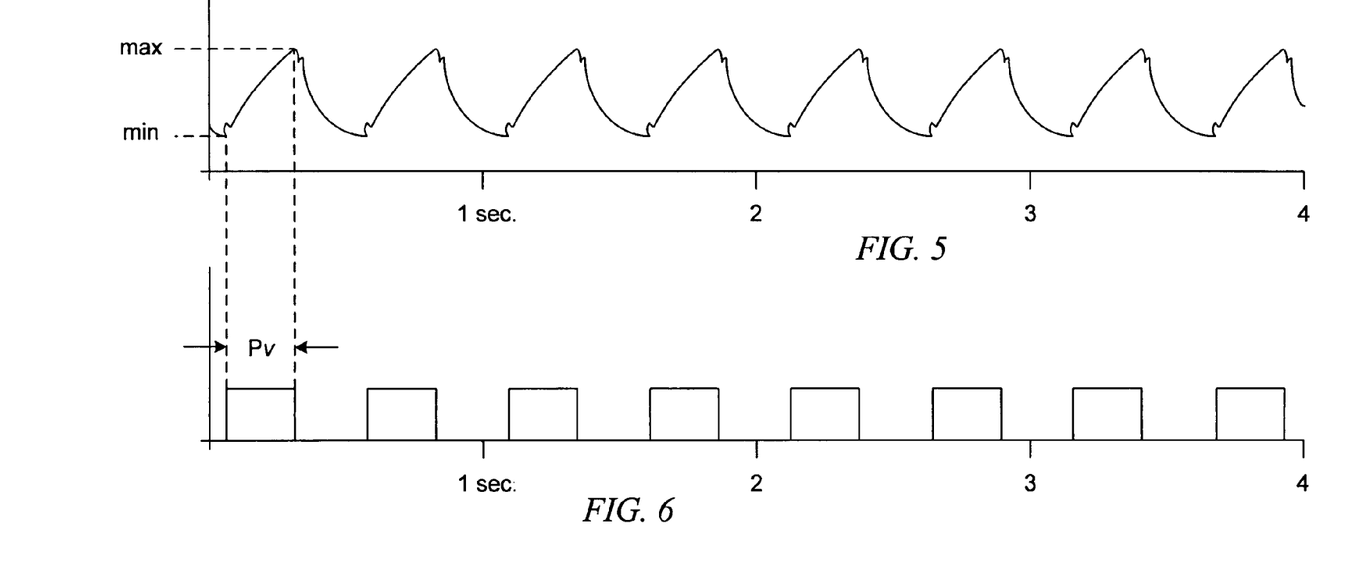
FIG. 5 is a graph of pressure vs. time, illustrating one example of an actual response of a programmable electric breast pump according to the invention.
FIG. 6 is a graph of voltage vs. time, illustrating one example of square wave input to a vacuum pressure relief valve in a system according to the invention.

FIG. 5 illustrates one example of an actual measured response of a programmable electric breast pump according to the invention. In this figure, the horizontal axis indicates time, and the vertical axis indicates vacuum pressure. A higher level in the vertical direction indicates greater vacuum, or equivalently, greater negative pressure. The response is a periodic vacuum pulse applied to the breast cups, where the maximum peak corresponds to the selected maximum vacuum level. The negative peak corresponds to a minimum vacuum level that may be pre-programmed, or that may be calculated as a function of the selected maximum. In this example, the breast pump controls (vacuum level selector 19 and vacuum rate selector 21) are set to synchronize the periodic vacuum pulse to the natural refractory time illustrated in the example of FIG. 4.

The periodic vacuum pulse as illustrated in FIG. 5 may be achieved by control circuit 69 actuating vacuum relief valve 67 each time vacuum sensor 65 senses a maximum or a minimum vacuum pressure. The square wave shown in FIG. 6 shows an example of an electronic pulse applied to valve 67 by control circuit 69 used to create the periodic vacuum pulse of FIG. 5. The duration of the electronic pulse applied to valve 67 lasts for a time period Pv, which corresponds to the duration of the rising edge of the periodic vacuum pulse, as shown. When vacuum sensor senses a maximum vacuum pressure in the breast cups, it sends a signal to control circuit 69 to remove the electronic pulse from valve 67, and the vacuum level drops until it reaches the minimum. At that point, vacuum sensor 65 alerts control circuit 69, and another electronic pulse is applied to valve 67. The frequency of the pulse in this example is approximately 120 cycles per minute. The maximum vacuum level is about 80 mmHg and the minimum vacuum level is about 20 mmHg. With such a control scheme, an electronic breast pump of the present invention maintains a vacuum pressure in the breast cups equal to or greater than the minimum level at all times. This ensures that sufficient suction is maintained in the breast cups to keep them in place against the breasts during a milking session.

Figure 7:
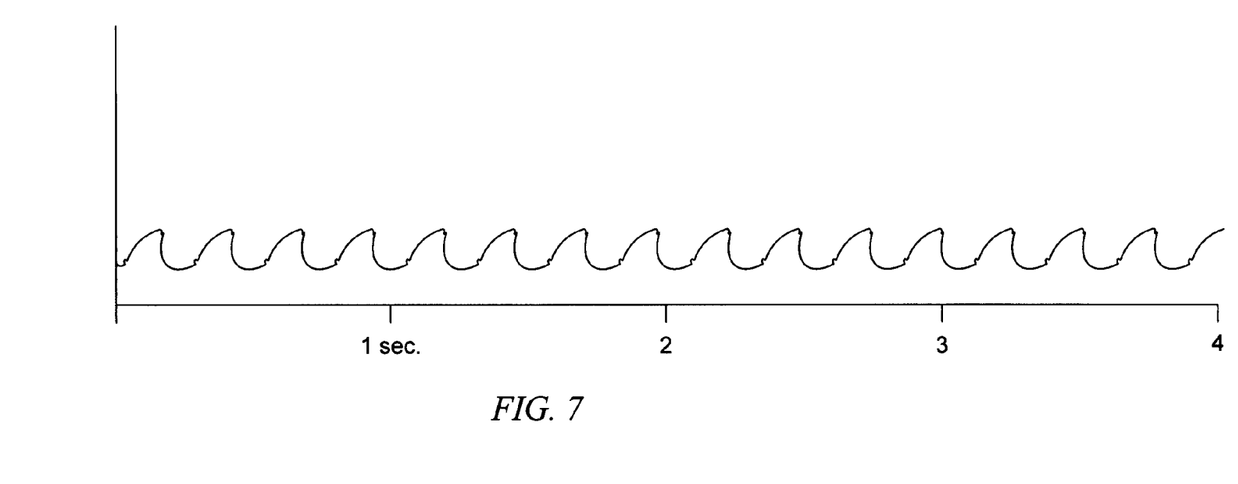
FIG. 7 is a graph of pressure vs. time, illustrating another example of an actual response of a programmable electric breast pump according to the invention.

FIG. 7 illustrates another periodic vacuum pulse achieved using the same breast pump, by changing the control setpoints. In this example, the frequency of the periodic vacuum pulse is as least twice that of FIG. 5. With the setpoint of vacuum rate selector 21 unchanged from its setting in FIG. 5, the new frequency may be achieved by lowering the maximum setpoint on vacuum level selector 19. By lowering the maximum setpoint for vacuum level, the maximum peak is achieved more rapidly, causing valve 67 to cycle more frequently. Lowering the maximum setpoint on vacuum level selector 19 may also result in a slight decrease in the minimum vacuum level calculated by control circuit 69. The overall result is a more rapid fluttering type of suckling cycle, where the suction is more gentle and ranges between about 18 mmHg and 35 mmHg. The suction cycle is about 240 cycles per minute.

Figure 8:
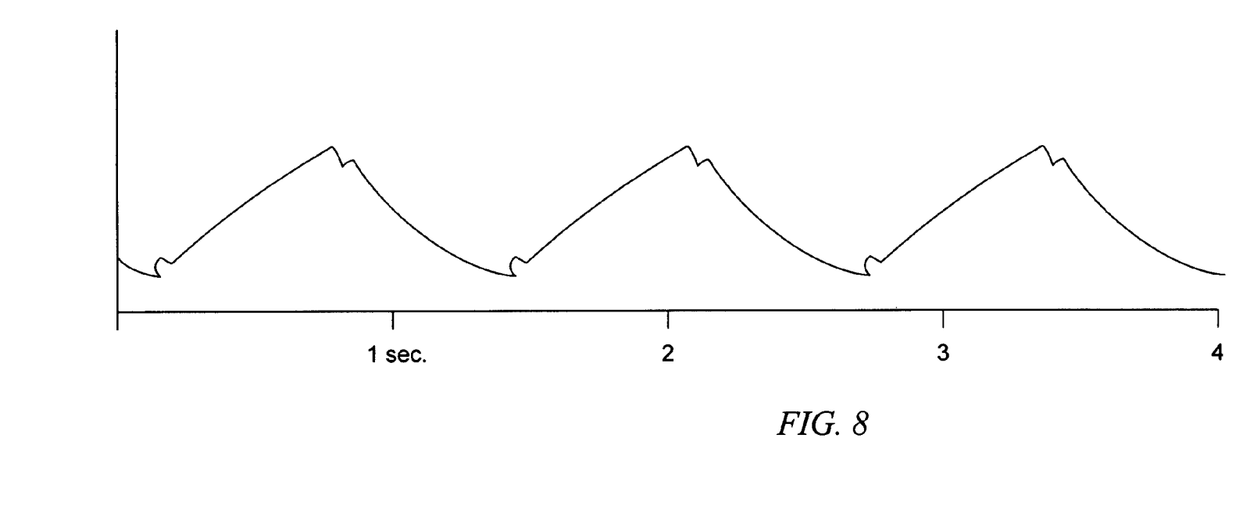
FIG. 8 is a graph of pressure vs. time, illustrating another example of an actual response of a programmable electric breast pump according to the invention.

FIG. 8 shows another periodic vacuum pulse that may be achieved by a user programming the controls of an electric breast pump according to the invention. In this example, the frequency of the periodic vacuum pulse is approximately 45 cycles per minute. One way of achieving this frequency is by leaving vacuum level selector unchanged from its position in the example of FIG. 5, and adjusting vacuum rate selector 21 to a lower level. As vacuum rate selector 21 is lowered, vacuum pump 51 slows down, and requires more time to achieve the maximum vacuum level in the breast cups, thereby lowering the frequency of the vacuum pulse. In addition, the amplitude of the vacuum pulse may be increased to a higher maximum level, which may also lower the vacuum pulse frequency. Adjusting vacuum level selector 19 to a higher level may also result in a slight increase in the minimum vacuum level calculated by control circuit 69. Thus, one or both of the manual controls 19 and 21 may be adjusted to achieve the pulse of FIG. 8. The overall result is a slower and deeper sucking cycle, which may range from about 25 mmHg to about 200 mmHg.

A programmable breast pump system according to the invention is not limited in operation to the foregoing examples of FIGS. 5-8. It should be readily appreciated that a user may adjust the vacuum level and vacuum rate controls to achieve a desired comfort level and/or tune the breast pump to the user's natural refractory time. The programmable controls also allow a user to make appropriate adjustments during a pumping session, for example, when the let-down reflex occurs, or as vacuum pressure requirements change as the session progresses.

Figure 9:
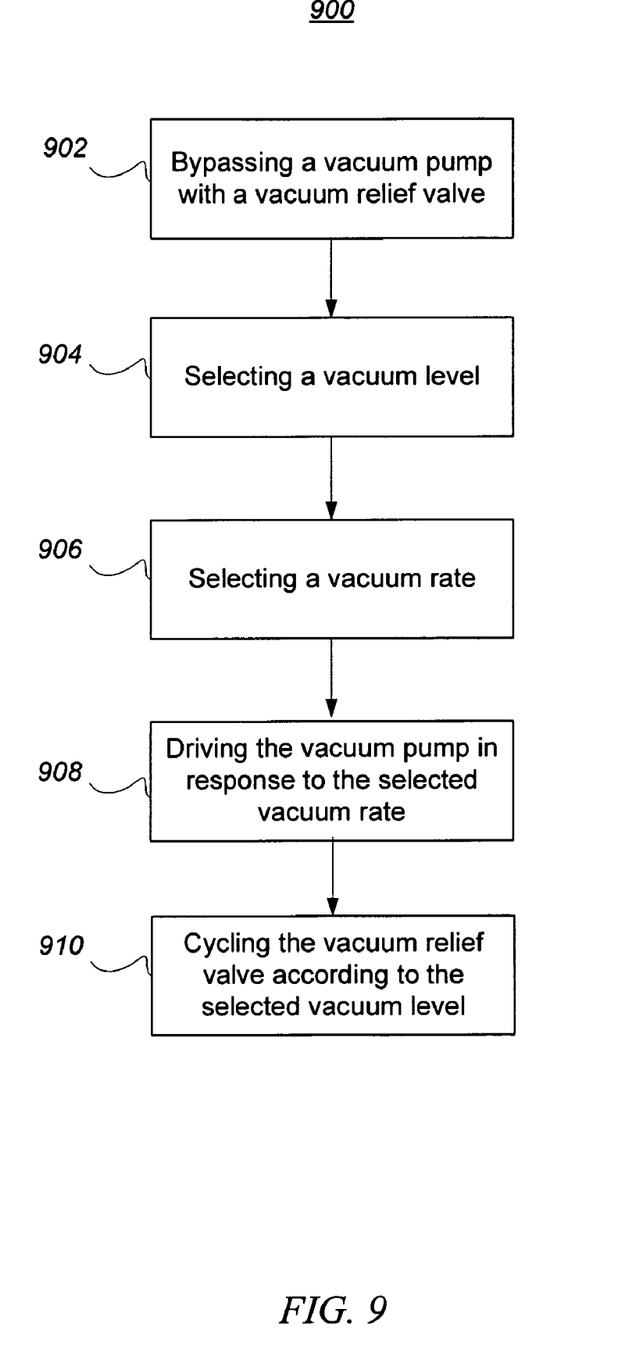
FIG. 9 is a process flow diagram of one embodiment of a method according to the invention for cycling vacuum pressure in a programmable electric breast pump.

The process flow chart of FIG. 9 illustrates one embodiment of a method 900 according to the invention for cycling vacuum pressure in a breast cup. In the process shown, it may be assumed that the breast cup chamber is pneumatically coupled to the inlet of a vacuum pump. The method begins with step 902, in which the vacuum pump is bypassed with a vacuum relief valve. In this step, bypassing the vacuum pump means that the vacuum relief valve is connected to the vacuum pump such that, when the valve is in one of two states (i.e. open or closed), the vacuum pump is not able to maintain a vacuum in the breast cup, and when the valve is in the other state, the vacuum pump is able to maintain or raise vacuum pressure in the breast cup.

The next step is step 904, in which a vacuum level is selected. In the next step 906, a vacuum rate is selected. These selecting steps 904 and 906 may be performed in any order. In one embodiment, either or both of these steps may be performed by a user adjusting the position of a manually operated selector. The selector may simply be toggled to an on position, or it may be adjusted to one of many possible positions. In another embodiment, selecting steps 904 and 906 may be performed automatically, for example, by a control circuit executing an algorithm.

Next, in step 908, the vacuum pump is driven in response to the selected vacuum rate. In one embodiment, the selected vacuum rate may correspond to the speed of a motor that is the prime mover for the vacuum pump. In the final step 910, the vacuum relief valve is cycled according to the selected vacuum level. In one embodiment, selecting the vacuum level in step 904 establishes a maximum setpoint for vacuum pressure in the breast cup. Then in step 910, the vacuum relief valve is actuated to relieve the vacuum pressure when it reaches the maximum. After a predetermined time period, the vacuum relief valve may be actuated again to allow vacuum pressure to build up. The predetermined time period may be set by a timing relay, or programmed, for example, in software executed by a control circuit. In this fashion, the vacuum relief valve is cycled according to the selected vacuum level. In another embodiment, selecting the vacuum level in step 904 establishes both a maximum and a minimum setpoint, allowing a controller to cycle the vacuum relief valve as vacuum pressure oscillates between the two setpoints.

Figure 10:
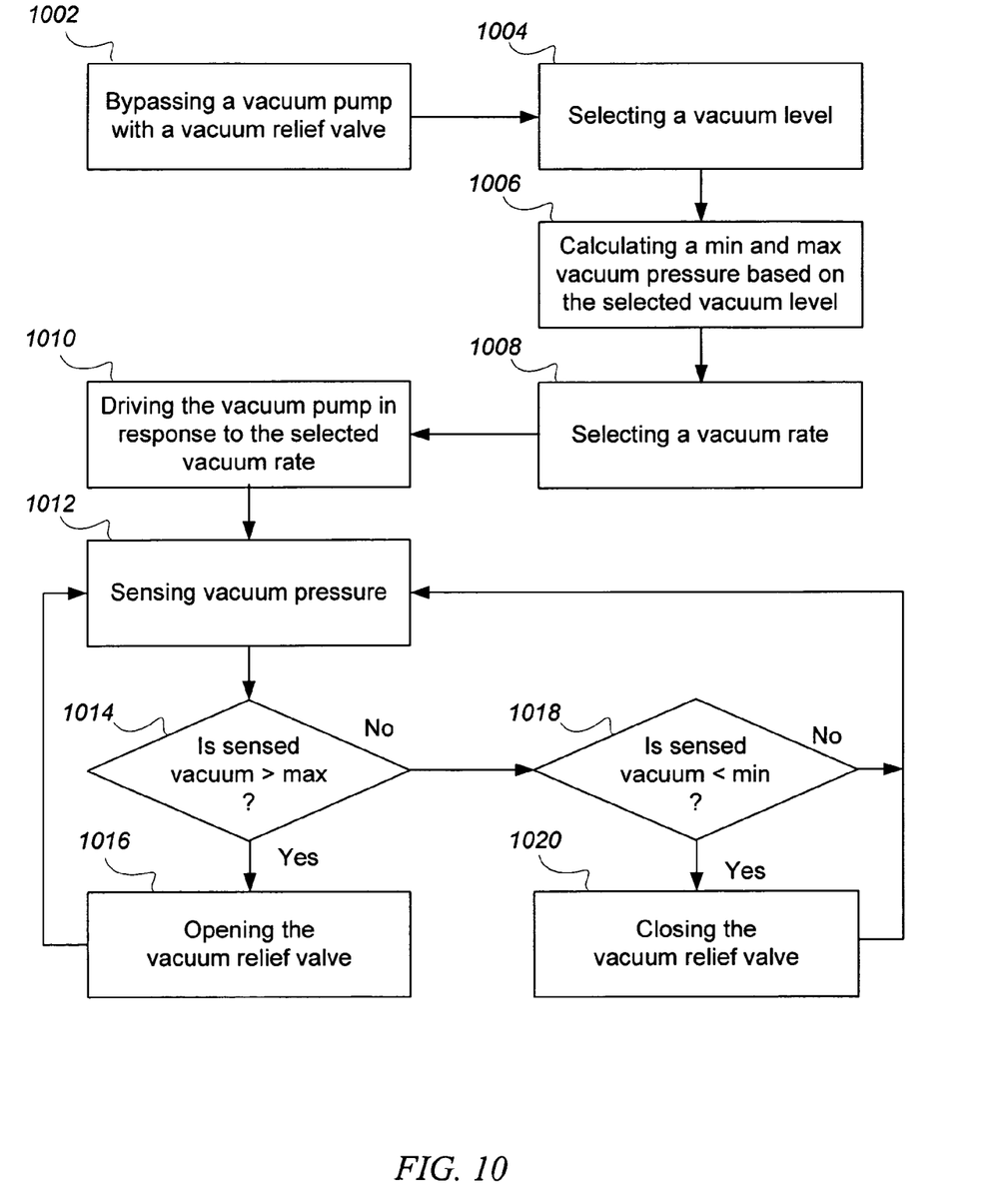
FIG. 10 is a process flow diagram of another embodiment of a method according to the invention for cycling vacuum pressure in a programmable electric breast pump.

FIG. 10 illustrates an embodiment of a method 1000 according to the invention, implicitly described in the context of the foregoing system embodiments, and provided here more explicitly in flow chart form. Method 1000 is a process for cycling vacuum pressure in a breast cup (or breast cup pair) that is pneumatically coupled to a vacuum pump. The method begins with step 1002, in which the vacuum pump is bypassed with a vacuum relief valve, as in step 902 of the previous embodiment. Next, in step 1004, a vacuum level is selected. This step may be performed using manual, automatic, or remote controls. In the next step 1006, a minimum vacuum pressure and a maximum vacuum pressure are calculated based on the vacuum level selected in the previous step. In one embodiment, the minimum and maximum levels may be calculated by a control circuit that executes an algorithm that is a function of variable input received from the selector. In another embodiment, the minimum level may be fixed at a predetermined value, while the maximum level may vary with the position of the selector. In another embodiment, the minimum and maximum levels change at different rates as the selected vacuum level changes.

The next step is step 1008, which is selecting a vacuum rate. This step may also be performed using manual, automatic, or remote controls. The next step 1010 is driving the vacuum pump in response to the selected vacuum rate. In one embodiment, this step is performed by varying the speed of a vacuum pump motor according to the selected vacuum rate, where a higher pump speed corresponds to a higher vacuum rate, and vice versa.

With the vacuum levels and vacuum rate selected, the method now progresses to its cycling steps. In step 1012, vacuum pressure is sensed in the breast cup(s). A decision block 1014 is then executed. In block 1014, it is determined whether the pressure sensed in step 1012 is greater than the maximum vacuum level. If so, the method continues on to step 1016. In step 1016, the vacuum relief valve is opened to relieve vacuum pressure, causing the vacuum pressure in the breast cup(s) to drop. The method then loops back to step 1012. If, however, in block 1014 it is determined that the pressure sensed in step 1012 is not greater than the maximum vacuum level, the method moves to step 1018.

Step 1018 is another decision block. It determines whether the vacuum level sensed in step 1012 is below the minimum vacuum level. If not, the method loops back to step 1012. If so, the method continues on to step 1020. In step 1020, the vacuum relief valve is closed, allowing vacuum pressure to build up in the breast cup(s). The method then loops back to step 1012.

Thus, once the process enters the cycling steps, it will follow a flow path through three possible process loops, where each process loop is initiated at step 1012 sensing a vacuum pressure. The first process loop occurs when the sensed vacuum pressure is greater than the calculated maximum level, in which case the method loops from step 1012 to 1014 to 1016 and back to 1012. The second process loop occurs when the sensed vacuum pressure lies between the calculated minimum and maximum levels, in which case the method loops from step 1012 to 1014 to 1018 and back to 1012. This loop may be executed any number of times in succession, as the vacuum pressure changes between its minimum and maximum setpoints. The third process loop occurs when the sensed vacuum pressure is less than the minimum level, in which case the method loops from step 1012 to 1014 to 1018 to 1020 and back to 1012. In this way, the process will cycle vacuum pressure in the breast cup(s) in a manner illustrated in FIGS. 5, 7 and 8. It should be recognized that steps 1014 and 1016 may be sequentially interchanged with blocks 1018 and 1020 without departing from the scope of the invention.

Figure 11:
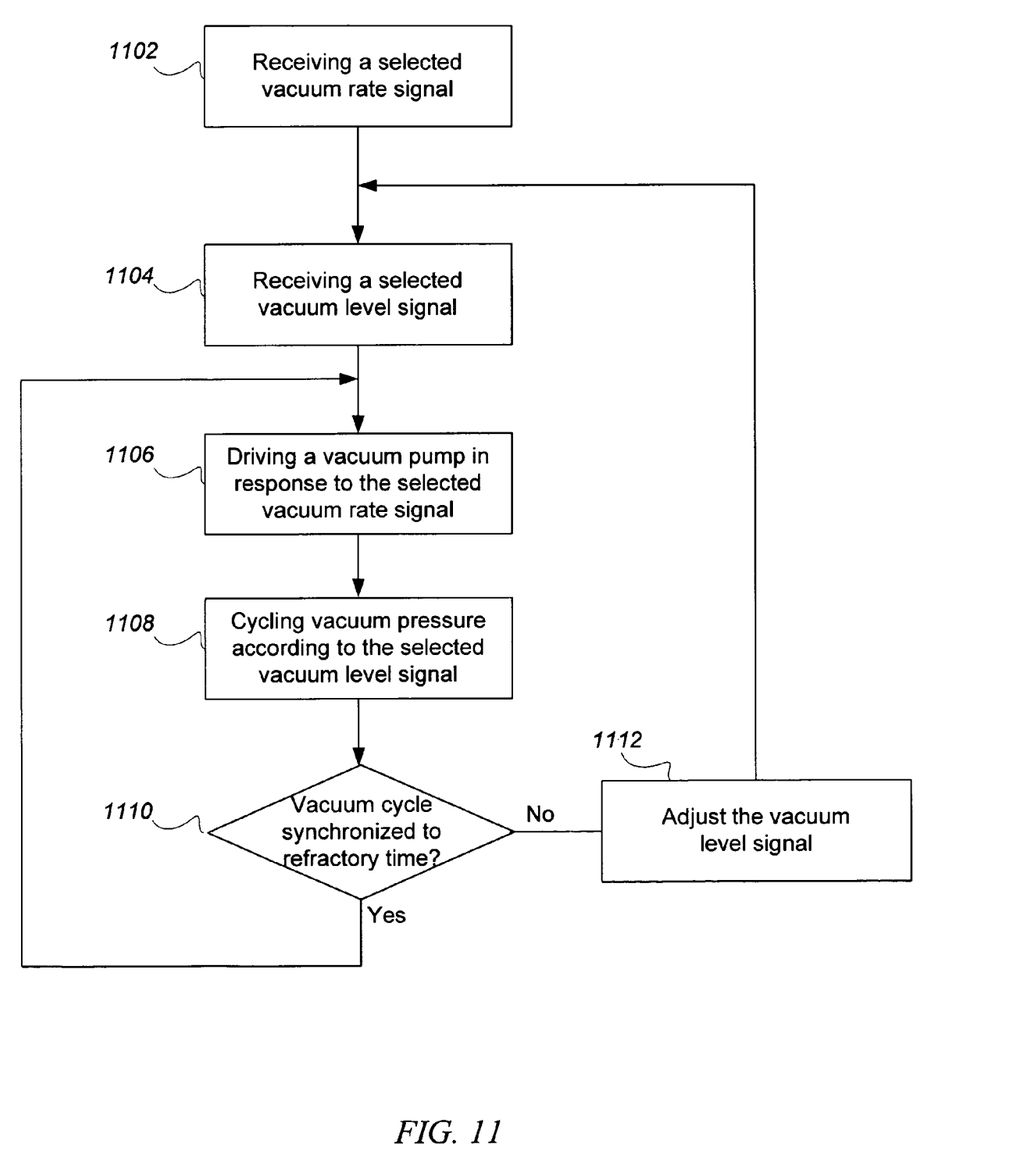
FIG. 11 is a process flow diagram of an embodiment of a method according to the invention for synchronizing cycling vacuum pressure in a programmable electric breast pump.

FIG. 11 illustrates a method 1100 according to the invention for synchronizing a breast pump with a natural refractory time of a breast. Method 1100 is an explicit process flow chart that captures another of many possible methods implicitly disclosed in the foregoing system embodiments. This method begins with step 1102, which is a step for receiving a selected vacuum rate signal. The next step 1104 is a step for receiving a selected vacuum level signal. Each of these first two steps may be performed by an automatic control circuit receiving input from a user manipulating a selector. The next step 1106 is driving a vacuum pump in response to the selected vacuum rate signal. This step may involve a control circuit issuing an output signal that controls the speed of the vacuum pump. Next, in step 1108, vacuum pressure is cycled in one or two breast cups that are pneumatically coupled to the vacuum pump. The cycling of the vacuum pressure is performed according to the selected vacuum level signal, as in previous embodiments.

In the next step, decision block 1110, it is determined whether the vacuum cycle is synchronized to, or in phase with, the natural refractory time. Preferably, this decision is resolved by the user according to her preference. If the vacuum cycle is not synchronized, the method progresses to a feedback loop through step 1112. In step 1112, the vacuum level signal is adjusted. The method then returns to step 1104. At step 1108, the vacuum pressure cycle changes according to the adjustment made in step 1104, i.e. adjusting the vacuum level signal in step 1104 changes the maximum and/or minimum setpoints, which, at a constant vacuum rate, changes the frequency of the vacuum pulse. Decision block 1110 may then be resolved again, and the feedback loop repeated as necessary until synchronization is achieved. At that point, the method loops back to step 1106, and the vacuum pump is driven according to the selected vacuum rate.

In another embodiment, steps 1102 and 1104 may be sequentially interchanged, in which case, step 1112 is provided to adjust the vacuum rate signal. In another embodiment, two adjustment steps may be included in the feedback loop, one for adjusting the vacuum level signal, and another for adjusting the vacuum rate signal. In this case, the feedback loop returns to step 1102.

It should be appreciated that the foregoing methods create an electronic refractory time in an automatic breast pump system by cycling a vacuum pulse according to a selectable vacuum rate and selectable vacuum levels. These features enable a user to program the breast pump for maximum comfort, or to synchronize the pulse of the breast pump with a natural refractory time to optimize the efficiency of a milk expressing session.

The invention has been disclosed in an illustrative style. Accordingly, the terminology employed throughout should be read in an exemplary rather than a limiting manner. Although minor modifications of the present invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for cycling vacuum pressure in a breast cup pneumatically coupled to a vacuum pump, the method comprising:

running the vacuum pump continuously;
bypassing the vacuum pump with a vacuum relief valve;
a user manually selecting a vacuum rate using a vacuum rate selector on a housing of the breast pump system;
the user manually selecting a minimum vacuum pressure using a vacuum level selector on the housing of the breast pump system;
maintaining a breast cup vacuum pressure in the breast cup equal to or greater than the minimum selected vacuum pressure at all times ensuring that sufficient suction is maintained in the breast cup to keep the breast cup in place against the breast during a pumping session;
the user manually selecting a maximum vacuum pressure using the vacuum level selector on the housing of the breast pump system;
driving the vacuum pump in response to the selected vacuum rate;
cycling the vacuum relief valve according to the selected minimum vacuum pressure and the selected maximum vacuum pressure;
the user observing the magnitude of felt vacuum in the breast cup during the pumping session and manually adjusting the vacuum level selector to maintain a comfortable level of vacuum during the pumping session; and
the user observing the resulting periodic cycling during the pumping session and manually adjusting the vacuum rate selector to maintain a desired pumping rate.

2. The method of claim 1 further comprising:
sensing vacuum pressure in the breast cup;
comparing the sensed vacuum pressure to the maximum vacuum pressure; and
opening the vacuum relief valve if the sensed vacuum pressure exceeds the maximum vacuum pressure.

3. The method of claim 2 further comprising:
comparing the sensed vacuum pressure to the minimum vacuum pressure; and
closing the vacuum relief valve if the sensed vacuum pressure is less than the minimum vacuum pressure.

4. The method of claim 1 further comprising filtering air drawn from the breast cup towards the vacuum pump for cycling vacuum pressure in a breast cup.

5. The method of claim 4 further comprising:
twice filtering air drawn from the breast cup towards the vacuum pump using sequentially residing first and second filters between the breast cup and the vacuum pump for cycling vacuum pressure in a breast cup;
measuring sensed vacuum pressure between the first and second filters; and
cycling the vacuum relief valve according to a comparison of the sensed vacuum pressure to the selected minimum vacuum pressure and the selected maximum vacuum pressure.

6. The method of claim 1 further comprising:
counting time elapsed during closure of the vacuum relief valve; and
stopping the vacuum pump if the time elapsed is less than a predetermined minimum closure time.

7. In an automatic breast pump system, a method for synchronizing a vacuum pump with a natural refractory time of a breast, comprising:
a controller receiving a selected vacuum rate signal manually selected by a user using a vacuum rate selector on a housing of the breast pump system;
a controller receiving a selected vacuum level signal manually selected by a user using a vacuum level selector on the housing of the breast pump system;
driving the vacuum pump responsive to the selected vacuum rate signal;
cycling vacuum pressure between a minimum vacuum and a maximum vacuum determined in the controller according to the selected vacuum level signal; and
adjusting the selected vacuum level signal until the vacuum pressure cycles in phase with the natural refractory time;
counting time elapsed during a single cycle of the breast pump system; and
stopping the vacuum pump if the time elapsed is less than a predetermined minimum time.

8. The method of claim 7 further comprising:
sensing a vacuum pressure; and
opening a valve bypassing the vacuum pump when the sensed vacuum level exceeds the selected vacuum level.

9. The method of claim 8 further comprising:
determining a vacuum pressure range based on the selected vacuum level signal;
comparing the sensed vacuum pressure to the vacuum pressure range; and
cycling the vacuum pump bypass signal to maintain vacuum pressure within the vacuum pressure range.

10. The method of claim 8 further comprising:
comparing the sensed vacuum pressure to a predetermined maximum vacuum pressure; and
stopping the vacuum pump if the sensed vacuum pressure exceeds the predetermined maximum vacuum pressure.

11. The method of claim 7 further comprising:
counting time elapsed since initially transmitting the drive signal; and
stopping the vacuum pump if the time elapsed exceeds a predetermined maximum running time.

12. The method of claim 7 further comprising:
sensing a temperature in the breast pump system; and
stopping the vacuum pump if the sensed temperature exceeds a predetermined maximum temperature.

13. A method for controlling a breast pump system for extracting milk by use of a breast cup, comprising:
providing a source of vacuum from a vacuum pump fluidly connected to the breast cup;
using a vacuum relief valve bypassing the vacuum pump to control the level of vacuum provided to the breast cup;
a user manually selecting a vacuum pump rate using a manual vacuum rate selector;
the user manually selecting a vacuum level using a manual vacuum level selector;
driving the vacuum pump in response to the selected vacuum pump rate;
cycling the vacuum relief valve between a minimum vacuum level and a maximum vacuum level determined from the selected vacuum level;
the user observing the magnitude of felt vacuum in the breast cup during the pumping session and manually adjusting the vacuum level selector to maintain a comfortable level of vacuum during the pumping session; and
the user observing the resulting periodic cycling during the pumping session and manually adjusting the vacuum rate selector to maintain a desired pumping rate;
sensing a temperature in the breast pump system; and
stopping the vacuum pump if the sensed temperature exceeds a predetermined maximum temperature.

14. The method of claim 13, wherein cycling the vacuum relief valve according to the selected vacuum level comprises closing the relief valve when a minimum vacuum level is reached and opening the relief valve when a maximum vacuum level based on the selected vacuum level.

15. The method of claim 14, further comprising sensing vacuum pressure in the breast cup.

16. The method of claim 15, further comprising:
receiving the sensed vacuum pressure in a controller;
comparing the sensed vacuum pressure to the maximum vacuum level in the controller; and
sending a signal from the controller to open the vacuum relief valve if the sensed vacuum pressure exceeds the maximum vacuum level.

17. The method of claim 16, further including:
comparing the sensed vacuum pressure to the minimum vacuum level in the controller; and
sending a signal from the controller to close the vacuum relief valve if the sensed vacuum pressure is less than the minimum vacuum level.

18. The method of claim 13, further comprising;
counting time elapsed on the timer in the controller between closing the vacuum relief valve and opening the vacuum relief valve; and
sending a signal from the controller to stop the vacuum pump if the time elapsed is less than a predetermined minimum closure time.

19. The method of claim 13, wherein selecting the vacuum level comprises the selecting a vacuum level using potentiometer.

20. The method of claim 13, wherein selecting the vacuum pump rate comprises selecting the vacuum pump rate using a potentiometer.

21. A method for synchronizing a breast pump suction cycle with a natural refractory time of a lactating breast, the method comprising:
turning the vacuum pump on, a vacuum relief valve bypassing the vacuum pump to control suction;
a user manually using a vacuum pump rate selector on a housing of the breast pump system to select a vacuum pump rate;
providing a vacuum pump rate signal from the vacuum pump rate selector to a microcontroller to control the vacuum pump rate;
the user manually using a vacuum level selector on a housing of the breast pump system to select a vacuum level;
providing a vacuum level signal from the vacuum level selector to the microcontroller;

setting a minimum vacuum pressure threshold and a maximum vacuum pressure threshold by the microcontroller based on the vacuum level selected by the user;
sensing a vacuum signal in at least one breast cup;
comparing the vacuum signal to the minimum vacuum pressure threshold and closing the vacuum relief valve if the vacuum signal is less than the minimum vacuum pressure threshold;
comparing the vacuum signal to the maximum vacuum pressure threshold and opening the vacuum relief valve if the vacuum signal is greater than the maximum vacuum pressure threshold;
the user manually adjusting at least one of the vacuum pump rate selector and the vacuum level selector to synchronize the breast pump suction cycle with the natural refractory time of a lactating breast; and
the user observing a let-down reflex during the pumping session and making manual adjustments to at least one of the breast pump during a pumping session when the let-down reflex occurs as the session progresses.

22. The method of claim 21, further including setting the minimum vacuum pressure threshold and the maximum vacuum pressure threshold by the microcontroller, based on a manually selected vacuum level signal to synchronize the breast pump suction cycle with the natural refractory time of a lactating breast.

23. The method of claim 22, wherein setting the manually selected vacuum level signal comprises:
increasing the minimum vacuum pressure threshold or decreasing the maximum vacuum pressure threshold to increase the frequency of the pump to synchronize the breast pump suction cycle with the natural refractory time of a lactating breast; and
decreasing the minimum vacuum pressure threshold or increasing the maximum vacuum pressure threshold to decrease the frequency of the pump to synchronize the breast pump suction cycle with the natural refractory time of a lactating breast.

24. The method of claim 22, wherein setting the minimum vacuum pressure threshold and the maximum vacuum pressure threshold comprises setting the minimum vacuum pressure threshold and the maximum vacuum pressure threshold by the microcontroller, based on the manually selected vacuum level signal and according to data stored in a lookup table.

25. The method of claim 22, wherein setting the minimum vacuum pressure threshold and the maximum vacuum pressure threshold comprises setting the minimum and maximum vacuum pressures by executing an algorithm.

26. The method of claim 21, further including:
counting time elapsed in a timer between closing the vacuum relief valve and opening the vacuum relief valve; and
stopping the breast pump if the time elapsed is less than a predetermined minimum closure time.

27. The method of claim 21, wherein manually selecting the vacuum pump rate signal comprises selecting a higher vacuum pump rate signal to increase the frequency of pumping and a lower vacuum pump rate signal to decrease the frequency of pumping to synchronize the breast pump suction cycle with the natural refractory time of a lactating breast.

28. The method of claim 21, further mapping the vacuum pump rate signal into a vacuum pump rate according to data stored in a lookup table to synchronize the breast pump suction cycle with the natural refractory time of a lactating breast.

29. The method of claim 21, further computing the vacuum pump rate by executing an algorithm using the vacuum pump rate signal as an input to synchronize the breast pump suction cycle with the natural refractory time of a lactating breast.

30. The method of claim 21, further including:
counting time elapsed in a timer while driving the vacuum pump; and
stopping the vacuum pump if the time elapsed exceeds a predetermined maximum running time.

31. The method of claim 21, further including stopping driving the vacuum pump if the sensed vacuum signal exceeds a predetermined maximum vacuum pressure.

* * * * *